United States Patent [19]
Billington

[11] 3,939,283
[45] Feb. 17, 1976

[54] COLORED FOODSTUFFS AND BEVERAGES
[75] Inventor: Arthur Ernest Billington, Watford
[73] Assignee: Beecham Group Limited, England
[22] Filed: Aug. 13, 1973
[21] Appl. No.: 387,750

[30]     Foreign Application Priority Data
         Aug. 19, 1972   United Kingdom............... 38787/72
         Oct. 5, 1972    United Kingdom............... 45943/72

[52] U.S. Cl. ........... 426/250; 426/540; 424/DIG. 5; 424/64
[51] Int. Cl.² ......................................... A23L 1/275
[58] Field of Search ............ 426/177, 250; 260/200

[56]            References Cited
           UNITED STATES PATENTS
    333,042   12/1885   Vallbrecht ...................... 260/200
  2,735,845    2/1956   Ruckstuhl et al.................. 260/200

OTHER PUBLICATIONS
Warner-Jenkinson, Code No. 5601–5701 1969.

*Primary Examiner*—Jeanette M. Hunter

[57]            ABSTRACT

An orange colouring material which is 1-(azo-benzene-4-sulphonic acid) -2-naphthol-6 8-disulphonic acid named "Orange AB" is effective as a colouring agent for foodstuffs and cosmetic compositions.

12 Claims, No Drawings

COLORED FOODSTUFFS AND BEVERAGES

This invention relates to edible colouring materials in particular for use in beverage and cosmetic compositions.

A compound suitable for inclusion into beverages as a colouring agent must have three requirements; it must have a good tinctorial power; it must be biologically acceptable; and it must be stable in the presence of fruit acids and strong reducing agents such as sulphurous and ascorbic acids which are commonly present in such compositions.

One orange dye which is commonly used for colouring beverages is colour index constitution no 16230 (C.I. Food Orange 4), commonly known as "Orange G" which is the disodium salt of 1-(phenylazo)-2-naphthol-6 8-disulphonic acid of formula (I):

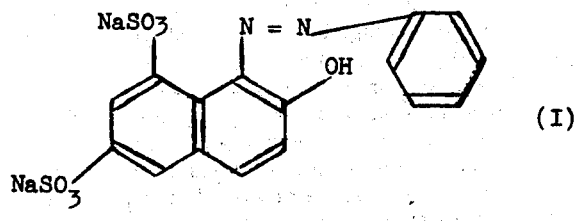

However one undesirable feature of Orange G is that it is now known to produce an increase in the level of Heinz bodies in the bloodstream when administered in high concentrations in the diet of test animals. These are bodies which appear in ageing red cells of the blood. As a result, Orange G is no longer suitable for universal unrestricted use in food. It has now been found that the compound of formula (II):

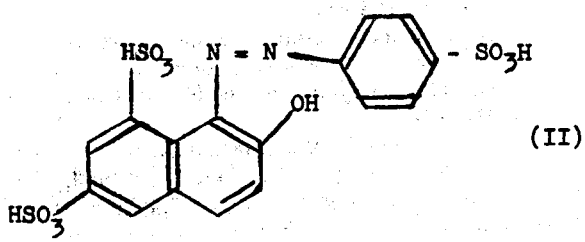

which is 1-(azo-benzene-4-sulphonic acid)-2-naphthol-6,8-disulphonic acid and its edible salts, are effective as orange colouring agents for foodstuffs or compositions intended for contact with the mouth for example lipstick composition. Compound (II) has a satisfactory tinctorial power in solution; is stable in acid conditions; and does not produce Heinz bodies in the blood.

The present invention therefore provides the compound 1-(azo-benzene-4-sulphonic acid)-2-naphthol-6 8-disulphonic acid and salts thereof.

We have named the compound of formula (II) "Orange AB" and it will be referred to as such throughout this specification.

From a second aspect the invention provides an edible composition comprising 1-(azo-benzene-4-sulphonic acid)-2-naphthol-6,8-disulphonic acid or an edible salt thereof together with an edible diluent.

The invention also provides an edible composition comprising an edible diluent or carrier in which 1-(azo-benzene-4-sulphonic acid)-2-naphthol-6,8-disulphonic acid or an edible salt thereof is incorporated as such.

By the term "incorporated as such" herein we mean that the compound itself is incorporated into the composition and not a precursor or derivative of the compound which may be transformed to Orange AB in situ.

Orange AB and/or its salts may be used to colour all types of edible materials which are intended for consumption or contact with the mouth. Suitable diluents and carriers which may be coloured include for example beverages such as soft drinks, fruit ades, wines, beverage concentrates such as syrups, powder concentrates or tablets; dietary type foods; ice creams sherberts and ices; ice milk products; bakery products; icings; confections for example boiled sweets, and confection toppings, syrups, jams and flavours; fruit gelatin desserts; cake mixes, meat products; cough syrups and other medicinal preparations intended for oral administration; dental preparations such as pastes, powders foams, mouth washes and similar oral antiseptic liquids; and cosmetic formulations in particular lipsticks.

Orange AB and its salts are particularly advantageous for use in colouring carbonated and non-carbonated soft drinks, and syrup concentrates which may be made up to such drinks.

Another composition from which the amount of organic colouring material is significant is a lipstick composition. We have found that orange AB is also useful for incorporation into lipstick compositions Accordingly the invention further provides a lipstick composition comprising 1-(azo-benzene-4-sulphonic acid)-2-naphthol -6 8-disulphonic acid or an edible salt thereof together with a suitable carrier.

The salts which may be included in the compositions of this invention may be the mono- di- and/or tri-salts of Orange AB Suitable salts for inclusion into beverages include alkalimetal salts of Orange AB, preferably the sodium salt. For lipstick compositions the compound is converted to an insoluble salt for example a barium or calcium salt.

Orange AB or its salts are incorporated in the material to be coloured in an amount required to attain the desired level of colouring. Preferred amounts of Orange AB for use in syrups cordials etc are 75 to 300mg/kg and in ready to drink beverages from 1–75mg/kg. Preferred amounts for use in lipstick compositions are from 1–10% by weight.

Orange AB may be conveniently obtained for example by coupling diazotized sulphanilic acid with 2-naphthol-6 8-disulphonic acid; or by a process described in British Patent No: 929,052 for the production of O-hydroxy azo compounds whereby the diazotate of 1-aminonaphthalene-6 8-disulphonic acid is reacted with the diazonium compound formed from sulphanilic acid.

The invention as illustrated by the following examples:

EXAMPLE 1

Preparation of 1-(azo-benzene-4-sulphonic acid)-2-naphthol-6 8-disulphonic acid.

Method 1

Sulphanilic acid (14.4g;00833 mole) and sodium carbonate (4.42g; 0.416 mole) were dissolved in water (330 ml) cooled to 0° then added with stirring to sodium nitrite (5.25g; 0.076 mole) in water (76 ml) at 0°. This solution in turn was added to 5N Hydrochloric acid (32 ml) at 0° then the resultant suspension was added rapidly to a solution of 2-naphthol-6 8-disulphonic acid, potassium salt (30g; 0.079 mole) and sodium hydroxide (10g; 0.25 mole) in water (125 ml) at 0°. After stirring for 30 mins. the solution was neutralised (pH 7.0) with 5N hydrochloric acid, then the water was removed on a rotary evaporator. The deep red solid was warmed on a steam bath with ethanol (600 ml) and water (150 ml) for 2 hours then the red solution was decanted and left in a refrigerator overnight. The precipitated dye was filtered off then dried at 68° in a vacuum oven. Yield= 33.5g (83% based on sulphanilic acid)

Method 2

30.3g of 1-aminonaphthalene-6, 8-disulphonic acid were diazotized in conventional manner with 64 ml of 5N hydrochloric acid and 6.9g of sodium nitrite. The diazonium compound was added at room temperature to 55 ml of 10N sodium hydroxide solution. After 2-3 minutes, 41g of sodium bicarbonate were added and substantially the diazonium solution prepared in usual manner from 17.3g of sulphanilic acid.

After a few hours, the hydroxyazo compound was isolated as described in method 1 above.

EXAMPLE 2

A ready-to-drink orange crush was prepared having the following composition:

| | |
|---|---|
| Orange Juice | 5% v/v |
| Sugar | 10% w/v |
| Citric Acid | 0.3% w/v |
| Saccharin Sodium | 0.01% w/v |
| Sodium Benzoate | 150 mg/kg |
| Colour:Orange AB | 38 mg/kg |
| Tartrazine | 10 mg/kg |
| Flavouring | q v |
| Carbonated water to | 100 % |

EXAMPLE 3

An orange squash for consumption after dilution was prepared having the following composition:

| | | |
|---|---|---|
| Orange Juice | | 25% v/v |
| Sugar | | 30% v/v |
| Saccharin Sodium | | 0.015% w/v |
| Citric Acid | | 1.2% w/v |
| Sulphur Dioxide | | 300 mg/kg |
| Colouring: | Orange AB | 10 mg/kg |
| | Tartrazine | 12 mg/kg |
| Flavouring | | q.v. |
| Water to 100% | | |

EXAMPLE 4

A lipstick composition was prepared as follows:

| | | |
|---|---|---|
| Base | Castor Oil | 69.50 |
| | Cocoa butter substitute | 14.00 |
| | Candelilla Wax | 9.00 |
| | Beeswax | 6.00 |
| | Carnauba Wax | 1.50 |
| | | 100.00 |
| Base | | 95% |
| 1-(azo-benzene-4-sulphonic acid) -2-naphthol-6 8-disulphonic acid | | 5% |

I claim:

1. A foodstuff or beverage composition comprising an amount of 1-(azo-benzene-4-sulphonic acid)-2-naphthol-6, 8-disulphonic acid or an edible salt thereof sufficient to impart to the composition the desired degree of orange color in combination with a foodstuff or beverage.

2. A composition according to claim 1 wherein 1-(azo-benzene-4-sulphonic acid)-2-naphthol-6, 8-disulphonic acid is incorporated.

3. A composition according to claim 1 wherein 1-(azo-benzene-4-sulphonic acid)-2-naphthyl-6, 8-disulphonic acid is combined with a beverage.

4. A composition according to claim 3 wherein the beverage is a carbonated or non-carbonated soft drink.

5. A composition according to claim 3 wherein the beverage is a syrup concentrate which may be made up to a soft drink.

6. A composition according to claim 3 wherein 1-(azo-benzene-4-sulphonic acid)-2-naphthol-6, 8-disulphonic acid is present in the form of the sodium salt.

7. A composition according to claim 4 in which the amount of 1-(azo-benzene-4-sulphonic acid)-2-naphthol-6, 8-disulphonic acid or edible salt thereof is 1–75 MG/KG.

8. A composition according to claim 7 wherein the amount is 25–50 MG/KG.

9. A composition according to claim 5 wherein the amount of 1-(azo-benzene-4-sulphonic acid)-2-naphthol-6, 8-disulphonic acid or edible salt thereof is 75–300 MG/KG.

10. A method of colouring foodstuffs and beverages which comprises incorporating therein an amount of 1-(azo-benzene-4-sulphonic acid)-2-naphthol-6, 8-disulphonic acid or an edible salt thereof sufficient to impart the desired degree of orange color thereto.

11. A composition according to claim 1 wherein the edible salt is an alkali metal salt.

12. A composition according to claim 11 wherein the alkali metal salt is the sodium salt.

* * * * *